United States Patent [19]
Linde

[11] Patent Number: 4,818,097
[45] Date of Patent: Apr. 4, 1989

[54] OCULAR-PURSUIT MEASURING

[76] Inventor: Lucille M. J. Linde, 1954 18th Ave., Greeley, Colo. 80631

[21] Appl. No.: 884,486

[22] Filed: Jul. 11, 1986

Related U.S. Application Data

[63] Continuation-in-part of Ser. No. 618,933, Jun. 8, 1984, abandoned.

[51] Int. Cl.$^4$ ............................................. A61B 3/00
[52] U.S. Cl. ................................. 351/203; 351/224; 351/239
[58] Field of Search ............... 351/224, 209, 210, 239, 351/202, 203, 205, 200, 246; 128/25 A

[56] References Cited

U.S. PATENT DOCUMENTS 2,451,932 10/1948 Ellis ...................................... 351/239
3,583,794 6/1971 Newman ............................ 351/210

Primary Examiner—Rodney B. Bovernick
Assistant Examiner—P. M. Dzierzynski
Attorney, Agent, or Firm—Dean P. Edmundson

[57] ABSTRACT

A unique technical process which must be taught is provided for quickly, simply, objectively and accurately measuring an individual's ocular tracking ability. The technique includes a process for measuring only the smooth movement of the eye, and both eyes together, in a neurologically oriented eye examination for educational diagnosis and evaluation. As a result of the examination one may prescribe motor-perceptual training. The most simple economical instrument providing instantaneously usable scores is described which is an improvement for this useful purpose and it overcomes the disadvantages of the prior art.

19 Claims, 2 Drawing Sheets 4,818,097

OCULAR-PURSUIT MEASURING

CROSS-REFERENCE TO RELATED APPLICATION

This application is a continuation-in-part of my co-pending application Ser. No. 618,933 now abandoned filed June 8, 1984.

FIELD OF THE INVENTION

This invention relates to measurement of a persons ocular tracking ability. More particularly, this invention relates to a technical process for measuring a person's ocular tracking ability and for diagnosing the need for motor-perceptual training for educational use.

BACKGROUND OF THE INVENTION

There is a great need for a quick objective evaluation of individuals to determine their ocular pursuit ability, which is a reflection of their neurological development. Such evaluation should not be a culturally biased test. The state of an individual's neurological development affects the person's learning efficiency as well as other abilities.

There has not heretofore been described a technique for the rapid, simple, and accurate objective evaluation of an individual's ocular tracking ability which is a result of the person's neurological development. Nor has there previously been provided a simple and effective way to objectively measure improvement in ocular pursuit ability in a short time following training.

SUMMARY OF THE PRESENT INVENTION

The present invention provides a process which is not obvious for a quick, simple, objective, and accurate measurement of an individual's ocular tracking ability. The process of this invention includes a neurologically oriented eye examination for educational diagnosis, evaluation, and prescribed training. This technical process eliminates guesswork in measuring a person's ocular pursuit ability.

The process involves, in part, the use of an ocular-pursuit measuring instrument comprising:

(1) a first upstanding leg member;
(2) a second upstanding leg member spaced from the first leg member;
(3) connecting means connecting the two leg members;
(4) vertically adjustable chin support means at the upper end of the first leg member, the support means being adapted to stably support the person's head during testing; and
(5) an arcuate member pivotably mounted at its midpoint to the upper end of the second leg member in a manner that the arcuate member may be pivoted about an axis passing through the midpoint perpendicular to the axis of the second leg member.

The arcuate member includes a graduated scale (preferably in one-half inch increments) extending outward from the midpoint along the arcuate member in both directions.

A target is moved along the arcuate member from the midpoint as far as smooth eye movement by such person following the target is completed accurately. That is, when eye movement becomes irregular (e.g., jerky, unable to focus on the target) the testing starts over again (at a lower starting point) and the target is moved outwardly from the midpoint and then back again in successively increasing distances until the second point of nystagmus is observed. The number of units (e.g., to the nearest half inch) between the midpoint of the arcuate member and the last or maximum point where smooth eye movement was completed accurately are then recorded, i.e., the farthest point of smooth eye movement is then recorded. This technical unique process is used on each eye individually and on both eyes together to determine each subtest score. Subtest scores are then totalled for one score.

The technique of the invention provides a means of indicating the general neurological health as reflected in results from ocular pursuit ability and enables treatment of the individual with motor perceptual training to improve neurological development and performance. It has also been found that an individual's ocular tracking score correlates beyond the 0.01 level of significance with the individual's score on the CTBS academic achievement test (California Test of Basic Skills).

The procedures of the present invention are useful and effective when used with individuals of all types, both for measuring and improving their ocular tracking ability and improving their neurological development. For example, individuals of the following types may be improved with the techniques of motor-perceptual training: (a) the learning disabled (e.g., those with hearing and visual impairment, mentally retarded, average, minority), (b) the motorially handicapped (e.g., those suffering from cerebral palsy, muscle spasms, epilepsy, scoliosis), and (c) those with special learning disabilities (e.g., aphasic, dyslexic) and gifted.

The ocular pursuit measuring instrument used in the practice of the present invention differs from conventional perimeters in basic respects. Conventional perimeters are used for medical purposes (e.g., by medical doctors) and evaluations are made by the examiner based upon what the subject says he sees. Normally a perimeter is used to measure the stationary eye, and each eye is measured separately. The purpose of perimetry is to ascertain the presence, position and nature of faults or lesions in the visual nerve apparatus. Accordingly, its use is of importance to the ophthalmological specialist.

The ocular pursuit measuring instrument used in the techniques of the present invention is used for educational purposes in evaluating and diagnosing an individual's ocular tracking ability. The examiner observes the moving eye and records the ability of the eye to follow a target without irregularity or jerkiness in eye movement. Then both eyes are tested together following a moving target.

Thus, the technique of this invention utilizes the ocular pursuit measuring instrument to obtain a neurologically oriented objective examination for educational diagnosis, evaluation, and prescribed motor-perceptual training. Because the examiner observes the moving eye(s), the examiner is able to determine accurately and quickly where smooth eye movement is interrupted by jerkiness or inability to focus on a target. Some perimeters require the use many items of equipment such as the use of lights, photographs, mirrors, and light beams. This ocular pursuit measuring instrument does not require any special equipment such as this.

Other advantages of the processes of the present invention are also apparent. There is no need for the examiner to communicate with the subject being examined other than to request the subject to follow the target with his eyes. Even very young subjects may be easily tested. The subjects do not have to be able to read in order to be tested in the process of the present invention. Also, the subject does not operate the instrument. Further, there is no need for specially equipped rooms for conducting the examination. Training of the examiner would not be time-consuming. The expertise develops through experience and sensitivity of the examiner in observing eye movement.

By using the process of this invention for measuring ocular tracking ability, motor-perceptual training has been demonstrated to improve oculomotor ability in as few as 5.5 to 7.5 hours of treatment with results at or beyond the 0.01 level of statistical significance.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
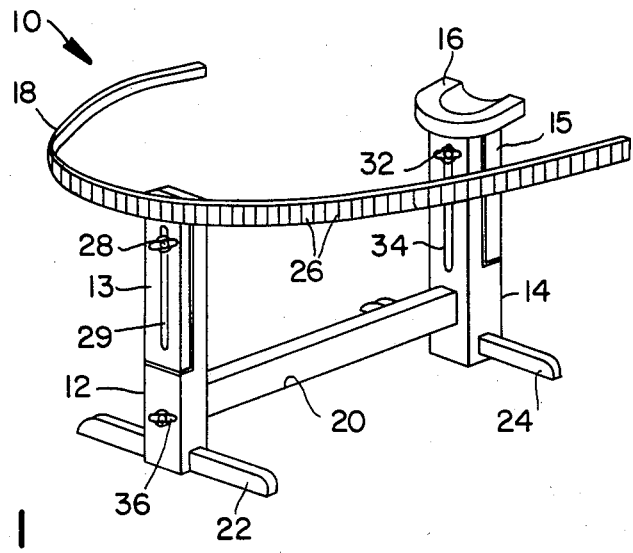
FIG. 1 is a perspective view of one embodiment of apparatus which is useful in the practice of the present invention.

One embodiment of the apparatus which is useful in the techniques and methods of the present invention is shown in FIGS. 1-4. The apparatus is portable and light-weight. No special equipment is required in order to utilize this apparatus. Thus, there is shown apparatus 10 comprising a first upstanding leg member 12 and a second upstanding leg member 14. The leg members are spaced apart from each other and are connected by means of bar 20 which holds the leg members securely in relative position. Leg member 12 includes foot member 22 and leg member 14 includes foot member 24 which are affixed to the lower ends of the leg members to stabilize them. Connecting bar 20 may be disconnected, if desired, by loosening nut 36 on a threaded bolt extending through leg member 12 and into bar 20. A similar nut and bolt assembly secures the opposite end of bar 20 to leg member 14.

Leg member 14 includes chin support means 16 at the upper end. The person being tested places his or her chin on the support so that the head is stabilized during testing. Arm 15 is vertically adjustable so that the apparatus may accommodate individuals of different height. One manner of providing vertical adjustment is to secure the chin support means 16 to the upper end of arm 15 which is secured to leg member 14 by means of bolt 32. Leg member 14 includes a vertical slot 34, as shown in FIG. 1. A wing nut on the inside end of bolt 32 may be loosened when it is desired to raise the arm 15.

Arcuate member 18 is pivotably attached at its midpoint to the upper end of leg member 12. A bolt (not shown) is secured at one end to member 18 and extends through leg member 12. The arcuate member 18 may be pivoted about its midpoint in one direction or the other for various testing procedures. The arcuate member may be mounted outside of leg member 12 (as shown in the drawings), or it may be mounted inside of leg member 12, if desired.

If desired, means may be included to permit vertical adjustment of the arcuate member. For example, as shown in FIG. 1, the arcuate member may be attached to arm 13 which includes vertical slot 29. Wing nut 28 on a bolt extending through arm 13 and leg member 12 may be loosened when it is desired to raise the arcuate member.

Arcuate member 18 includes a graduated scale along its periphery which is readable by the person conducting the testing. The scale may include any desired graduations 26, although it has been found that a tape measure having one-half inch graduations is very useful for the techniques of the present invention.

The size of the arcuate member may vary, although it has been found that a radius of curvature of the arcuate member is preferably in the range of about 20 inches. The arcuate member is preferably semi-circular.

In order to measure the ocular tracking ability of a person using the instrument shown in the drawings, the person places his or her chin on the chin support 16 and faces the arcuate member 18. Initially the arcuate member is placed in horizontal position (as shown in FIG. 1). The person conducting the testing then requests the subject to follow a target with the eyes as the target is moved along the arcuate member away from the midpoint. When the subject's smooth eye movement in following the target is interrupted (i.e., when it becomes jerky or irregular) then a notation is made as to the distance to the nearest half inch that the eye has moved from the midpoint of the arcuate member with smooth eye movement. The test is then repeated moving the target away from the midpoint in the opposite direction. The test is preferably done with each of the subject's eye separately and then with both eyes together.

When testing a subject, if no nystagmus is noted as the target is moved along the arcuate member of the measuring instrument, then the result is a perfect score for that particular sub-test. On the other hand, if no smooth eye movement is noted, then a zero score is recorded.

It often happens that an individual may be able to work through the first point of nystagmus. Thus, when testing a subject and the first point of nystagmus is reached, it is necessary to begin the testing again from the midpoint of the arcuate member. The target is repeatedly moved farther outward each time and back to the midpoint each time. This process is repeated by increasing the distance which the target is moved (e.g., by 0.5 inch) until the second point of nystagmus is reached. The second point of nystagmus may be farther than the first point where nystagmus is noted.

When the second point of nystagmus is reached, that particular subtest is stopped and the last perfect score is recorded. That is, the last distance (e.g., in 0.5 inch increments) at which smooth eye movement was completed accurately is recorded. This can be checked again for accuracy if desired by repeating the last testing point to verify that it is accurate. By using this technical process a valid score is obtained which is useful for statistical research.

Figure 2:
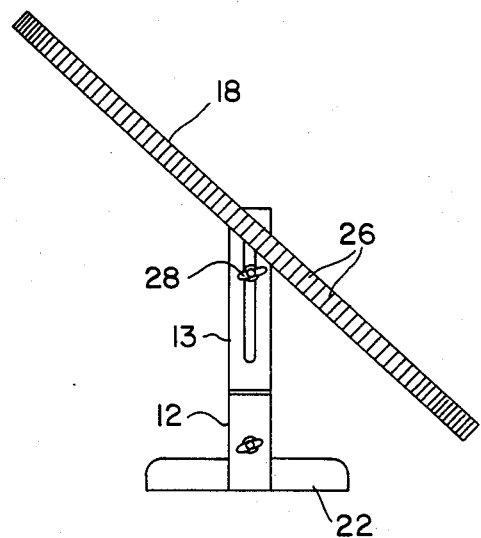
FIG. 2 is a front elevational view of the apparatus shown in FIG. 1 showing one manner in which the arcuate member may be tilted during testing.
Figure 3:
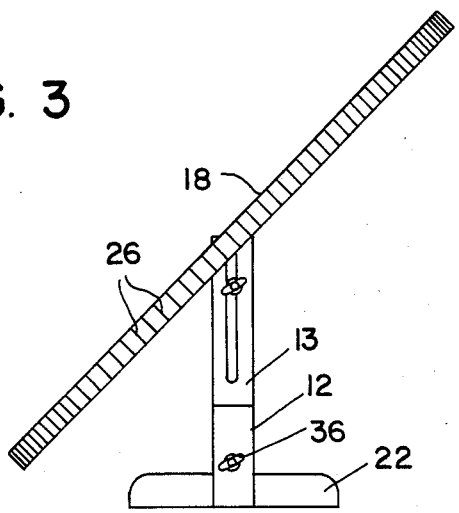
FIG. 3 is a front elevational view of the apparatus shown in FIG. 1 showing another manner in which the arcuate member may be tilted during testing.

The testing is then repeated as explained above after tilting the arcuate member away from horizontal. For example, as shown in FIG. 2, the arcuate member is tilted in one direction at a 45° angle for additional testing. Then the arcuate member is tilted in the other direction, as shown in FIG. 3, for additional testing.

Figure 4:
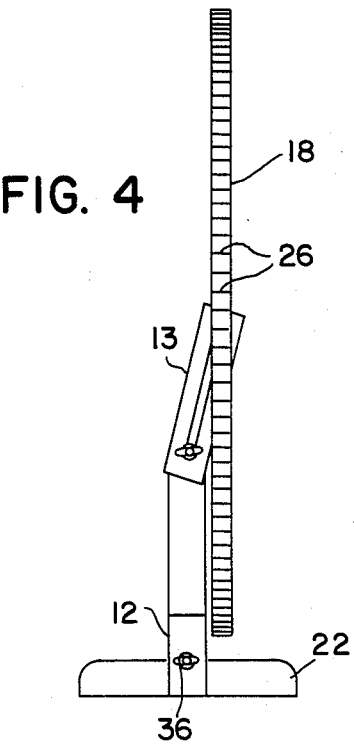
FIG. 4 is a front elevational view of the apparatus with the arcuate member in vertical position.

As shown in FIG. 4, it is also possible to pivot the arcuate member 18 to a vertical position for additional testing, if desired. In order to do this, arm 13 is raised relative to leg 12 and then tilted slightly to one side so that arcuate member 18 may be placed in true vertical position.

Figure 5:
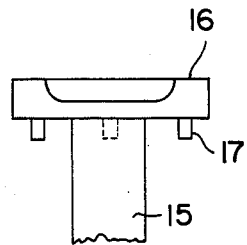
FIG. 5 shows one manner in which the chin support means is adjustable.

As shown in FIG. 5, chin support 16 includes attachment means which enables it to be secured to the top of arm 15 in three different positions. Thus, pegs 17 carried by the underside of chin support 16 are spaced apart and are each adapted to be received in a slot or opening in the top of arm 15. The center peg is used when the arcuate member is in the positions shown in FIGS. 1–3. When the arcuate member is in the position shown in FIG. 4, the chin support is moved to the left so that the midpoint of the arcuate member is aligned between the position of the subject's eyes.

The simplicity and precision of obtaining accurate measurements make the ocular-pursuit measuring instrument a valuable tool for a reliable and accurate objective examination to determine a subject's ocular tracking ability. Evaluation of a subject may require only a few minutes (usually 5 to 25 minutes), and the test score is not culturally biased. Yet, the instrument is precise enough to detect improvement in a subject's ocular tracking ability after a short term of motor-perceptual training (in as little as four weeks after training has started). Use of this instrument eliminates guesswork in determining a subject's ocular tracking ability. The examination may be termed a neurologically oriented eye examination which is valuable for educational diagnosis and evaluation.

The instrument described herein may be made of light weight materials (such as wood, for example) and carried to class rooms or offices. It can be easily disassembled. It is also inexpensive, and there are few moving parts.

In the instrument shown in the drawings the arcuate member is mounted ahead of the leg member 12 closest to the examiner. In an alternative embodiment the arcuate member may be mounted on the opposite side of the leg member 12 (i.e., on the side toward the subject). With either design the distance between the arcuate member and the subject should be 20 inches, for comparative results.

The examination of the subject determines the motility ability of the eye starting from the midline (i.e., the center point between the two eyes). A target (for example, a colored tip on the end of a pointer) is moved outwardly from the midpoint of the arcuate member in the horizontal plane and then back to the mid-point. The target is moved left from the mid-point for the left eye and is moved right from the mid-point for the right eye. A "best" rating is 18 inches for one eye. A score of "0" is recorded if the person is unable to track at any distance. When both eyes are tested together, the target is moved from the mid-point in one direction and then back through the mid-point in the opposite direction. A "best" rating for both eyes is 36 inches. The arcuate member is then tilted to a diagonal position (e.g., 45° from horizontal) and the same testing procedure is followed, except that the target is moved only nine inches in each direction from the mid-point of the arcuate member. Then the arcuate member is pivoted to the diagonal position from left to right. It may also be placed in the vertical position and the test is continued, moving the target nine inches in each direction from the mid-point of the arcuate member.

Before the examination is begun the subject is seated comfortably at the instrument with the head resting on the chin support means. This prevents the subject from moving his or her head during the examination. The instrument and subject are positioned such that the subject faces away from windows or strong lights or other distractions. When one eye is being tested the other eye is covered.

During the examination the subject is requested to focus on the target and to follow the moving target as far as possible along the arcuate member until the eye wavers or jerkiness of motion occurs or until the subject is unable to focus on the target. Blinking is permissible.

It has been found that ocular tracking ability, as measured and described herein, is highly correlated with a student's academic achievement ability. Those students whose ocular tracking scores indicate need for improvement may then be given motor-perceptual training. In order for individuals to function at optimum levels the sense modules must be functioning adequately to assure complete and accurate input to the nervous system.

The technical process of this invention is useful with respect to persons of all ages and educational backgrounds, although for statistical purposes individuals with known dysfunctions (such as cross-eye or midline problems) should be omitted. This type of individual, however, improves with motor-perceptual training.

The diagnostic value of ocular tracking ability measurements with the instrument described herein is that individuals of any age or developmental level who require improvement in ocular tracking ability, which has been found to correlate significantly with learning efficiency, may be quickly and easily identified. Prescribed motor-perceptual training may be expected to ameliorate neurological dysfunction and help organization on the motor-perceptual-conceptual-social-emotional levels. When the neural circuits are improved (as indicated by improved ocular tracking ability) all activities directly related to such efficiency may be expected to improve. Many other developmental disabilities and/or handicaps may also be helped as a result of the motor-perceptual training.

The usefulness of the techniques of the present invention are further illustrated by means of private research providing the following examples.

EXAMPLE 1

This example illustrates a presently preferred process for testing smooth eye movement of a subject in accordance with the present invention. The apparatus used for the testing is as illustrated in the drawings.

(a) Testing is begun from the mid-line or mid-point position of the individual with the head on the chin rest in relation to the arcuate member of the measuring instrument, which allows the line of vision at "0" on the arcuate member to be a center position between the eyes.

(b) A colored object (e.g., a tangerine color) is moved out (for example, horizontally for one eye for one subtest) along the arcuate member, starting from the "0" position, to 15 inches (for example) until the first point of nystagmus or wavering of the eye is noted. A score is not yet recorded. The test is begun again at "0" and proceeds to a lesser distance (perhaps 14 inches) and then back to "0" again. If eye movement is performed smoothly in this portion of the test, then the test is begun again at "0" and proceeds for one-half inch more (say, to 14.5 inches) and then back to "0". If eye movement is smooth in this portion of the test, then the test is run again from "0" to 15 inches and then back to "0". If eye movement is now smooth up to 15 inches, the test indicates that it was possible to work through the first wavering. Then the test is performed up to 15.5 inches and back to "0". If eye movement is smooth the testing continues to distances up to 18 inches horizontally in each direction (left, right or both) or until nystagmus is observed. For example, if nystagmus is noted at 17 inches, then a score of 16.5 inches is recorded (i.e., the maximum distance the eye moves before nystagmus is observed). The purpose is to record only the perfect or smooth movement of the eye(s). When conducting the testing it is possible, for example, to use a rubber band on the arcuate member to mark the positions of eye movement during the testing. The rubber band is moved after each try, usually 0.5 inch at a time. Although the arcuate member as illustrated is divided or marked into 0.5 inch segments, other graduations may instead be used, if desired.

(c) The foregoing describes only one sub-test (i.e., along a horizontal path for one eye). The same procedure is followed for other sub-tests along other meridia. Testing consists of observing the eye horizontally 18 inches to the right from center for the right eye (subtest 1); horizontally 18 inches to the left from center for the left eye (subtest 2); horizontally 18 inches to the right and left from center for both eyes for a total of 36 inches (subtest 3). The testing may continue farther in one direction than the other in any test to which this pertains. Other subtests are as follows: diagonal testing, left to right, 9 inches from center, a total of 18 inches up and down for one eye (subtest 4); diagonal testing, right to left 9 inches from center, a total of 18 inches up and down for the other eye (subtest 5); diagonal testing, left to right, 9 inches from center, a total of 18 inches up and down with both eyes (subtest 6). If nine subtests are desired, one may use the same procedure as described above except include measuring in the opposite direction for each eye and both eyes together.

EXAMPLE 2

A survey was conducted with a random sample of twenty-four seventh grade students. The purpose of the study was to determine if there was any significant correlation between the grade point average of the twenty-four subjects and their measured ocular tracking ability which was measured to the closest one-half inch for a total of nine subtests using the ocular tracking measuring instrument described herein. A resulting score from three subtests on the total for both eyes, and a total horizontal score, were also analyzed statistically in the event a shortened test would be useful. A re-test was given to thirteen of the twenty-four subjects and analyzed for the total scores, total for both eyes, and a total horizontal score.

All of the statistical correlations were significant at the 0.01 level of alpha and are as follows:

1. The correlation of the total scores (nine subtests) with the grade point averages (GPA) was 0.81. The mean GPA was 2.89 (SD=0.82); and the average total ocular score was 132.06 (SD=32.9).
2. The correlation of the total scores for both eyes (three subtests) with the GPA was 0.75. The means GPA was 2.85 (SD=0.82); and the average total ocular score was 58.35 (SD=12.41).
3. The correlations of the total for horizontal scores (three subtests) with the GPA was 0.80. The mean GPA was 2.88 (SD=82); and the average total horizontal score was 46.04 (SD=14.9).

Correlation of Test and Re-test:
1. A test-retest comparison of the total ocular scores of subjects (nine subtests) yields a coefficient of stability of 0.74. The average ocular score for Test I was 141.42 (SD=35.93); and for Test II 138.96 (SD=37.17).
2. The test-retest comparison of the total scores for both (three subtests) yields a coefficient of stability of 0.92. The average ocular score for Test I was 61.58 (SD=15.08) and 59.5 (SD=13.58) for Test II.
3. The test-retest comparison of the total horizontal scores (three subtests) yields a coefficient of stability of 0.90. The average ocular score for Test I was 49.27 (SD=17.49) and 57.38 (SD=15.48) for Test II. This was significant at 0.005 level of alpha.

The results indicated by these statistical correlation data make evident that there is a very high correlation between the academic grade point average of the subjects (academic classes of math, English and social studies) and the scores of ocular tracking ability. The information obtained in the study is useful for educational purposes as a basis for action in curriculum planning to provide a motor-perceptual training program to enable students to reach their full potential. This type of training should be provided prior to other remedial training.

EXAMPLE 3

A study was conducted to determine if there was any significant improvement of students in ocular tracking ability as the result of a motor-perceptual training program. Twenty-one students were in the experimental group which received the treatment for one forty-five minute class period one day per week for seven weeks. Matched to this group was a control group of twenty-one students who did not receive any training. A pre-test, and post-test after training, were given to the experimental group, and to the control group, also. Scores were then statistically analyzed by a statistician. The statistical results are as follows:

The control group improved 47 inches with a mean gain score of 2.24 (SD=12.51). The experimental group improved 895.5 inches with a mean gain score of 42.64 (SD=16.60). The obtained t-statistic was negative 8.69 which showed statistical significance beyond the 0.01 level (p 0.00001).

These data provide strong statistical evidence that motor-perceptual training does in fact improve ocular tracking ability.

Included in this study was a group of twenty-eight students comprised of eighteen of the controls with available CTBS scores and ten additional students. The purpose of this study was to determine the relationship between ocular tracking ability (six subtests) and achievement scores on the CTBS standardized achievement test.

Several statistical correlations were analyzed comparing the CTBS with ocular tracking ability for nine, six, and three subtests; and test-retest results are provided for twenty of the twenty-eight subjects for six and nine subtests. The statistical correlations and the significance levels for the statistical data are presented as follows:

1. The correlation of the total scores (nine subtests) with the CTBS was 0.41. The mean ocular tracking score was 140.52 (SD=29.31); and the CTBS mean average score was 4.56 (SD=1.88). Statistically significant at the 0.05 level.
2. The correlation of the total scores (six subtests) with the CTBS was 0.43. This coefficient is statistically significant at the 0.02 level of alpha. The mean ocular tracking score was 91.77 (SD=24.68); and the mean CTBS score was 4.56 (SD=1.88).
3. The correlation of the total horizontal ocular tracking ability score (three subtests) and the CTBS was 0.45. The mean ocular tracking score was 45.02 (SD=17.58); and the mean CTBS score was 4.56 (SD=1.88). Significant at the 0.01 level.
4. The test-retest correlation of the total ocular tracking scores (nine subtests) of the control subjects between Test I and Test II for the twenty subjects yields a coefficient of stability of 0.87. The mean average ocular score for Test I was 136.88 (SD=31.45); and the mean average score for Test II was 134.88 (SD=32.13). Significant beyond the 0.01 level (p 0.001).
5. The test-retest correlation of the total ocular tracking scores (six subtests) between Test I and Test II for the twenty control subjects yields a coefficient of stability of 0.88. The mean ocular tracking score was 88.9 for Test I (SD=25.63), and 92.88 (SD=25.87) for Test II. Significant beyond the 0.01 level.

A clear positive relationship exists between the total ocular tracking scores and the California Test of Basic Skills grade equivalent scores for the twenty-eight subjects. The data for the total nine ocular tracking scores and three total horizontal ocular tracking scores corroborates the findings when ocular tracking scores for six subtests were correlated with the CTBS. The test-retest data provides stability for the examination when Test I was compared with Test II.

EXAMPLE 4

A study was conducted with forty-one students in a motor-perceptual training program; and statistical comparisons were made between thirty-one of such students in an experimental and another thirty-one students in a control group. Students were from first, second and third grades.

The purpose was to determine the extent of improvement in visual-pursuit ability, academic achievement, or other abilities of students following motor-perceptual training. Experimental and control students were matched in terms of academic achievement. There were ten students in the original group of forty-one which could not be matched academically with control students and those ten were consequently not used.

Students in the experimental group were given a comprehensive motor-perceptual training program on a once per week basis for ten weeks. Control students received no motor-perceptual training.

The oculomotor results were unequivocal. The results were self-evidence that motor perceptual training does improve ocular tracking ability in a relatively short period of time (one 45 minute class period one day per week for 7-10 weeks; approximately ten minutes of the class time was devoted to ocular tracking activities).

The ocular tracking ability gain for the forty-one students who were given motor-perceptual training averaged almost 56 inches. All of the students measured some improvement on all six subtests.

Students in the experimental group did better than the control group on the CTBS Posttest a total of 575 points for twenty-five students, a mean score of 23.

Six students in the control group did better than those in the experimental group on the CTBS Posttest a total of 109 points. This represents a mean score of 18.17.

The criterion used in the measuring of academic achievement gains for the two groups was the posttest of the California Test of Basic Skills (a standardized test).

A t-test was conducted comparing mean scores of the two groups on posttest scores of the CTBS. The resulting t-ratio was 3.128 which is significant beyond the 0.01 level. The results show that motor-perceptual training helps students in the experimental group to do better on the CTBS than students in the control group who did not participate in the program.

It was observed that the students in the experimental group improved noticeably in coordination ability.

What is claimed is:

1. A technical process for measuring the ocular tracking ability of a person comprising the use of the following
   (a) providing an ocular-pursuit measuring instrument comprising:
      (i) a first upstanding leg member;
      (ii) a second upstanding leg member spaced from the first leg member;
      (iii) connecting means connecting said first and second leg members;
      (iv) vertically adjustable chin support means at the upper end of said first leg member, said support means being adapted to stably support said person's head; and
      (v) an arcuate member pivotably mounted at its midpoint to the upper end of said second leg member in a manner such that said arcuate member may be pivoted about an axis passing through said midpoint perpendicular to the axis of said second leg member; wherein said arcuate member includes a graduated scale therealong;
   (b) positioning such person in a manner such that the person's chin is stably supported by said chin support means;
   (c) placing said arcuate member in a horizontal position;
   (d) testing the person's ocular tracking ability by moving a target along said arcuate member from said midpoint to measure smooth eye movement by such person following said target; and
   (e) recording the number of units on said graduated scale between said midpoint and the maximum point where smooth eye movement was completed accurately.

2. A process in accordance with claim 1, wherein step (d) comprises:
   (i) moving said target along said arcuate member from said midpoint until a first point of nystagmus is observed;
   (ii) returning said target to said midpoint;

(iii) moving said target along said arcuate member from said midpoint, while measuring smooth eye movement, to a point which is less than said first point of nystagmus;
(iv) returning said target to said midpoint;
(v) moving said target along said arcuate member from said midpoint, while measuring smooth eye movement, to a point which is one graduated unit farther than the point reached in step (iii);
(vi) repeating steps (iv) and (v), increasing the distance said target is moved along said arcuate member by one graduated unit with each repetition until a second point of nystagmus is reached.

3. A process in accordance with claim 1, wherein said arcuate member is semi-circular and has a radius of curvature in the range of about 20 inches.

4. A process in accordance with claim 1, wherein said scale on said arcuate member is graduated in units of one-half inch from said midpoint outwardly therealong.

5. A process in accordance with claim 1, wherein said first and second leg members are parallel to each other and are spaced from each other such that the distance between the subject and the arcuate member is about 20 inches.

6. A process in accordance with claim 1, wherein said ocular tracking ability of such person is tested (a) with said arcuate member in horizontal position, (b) with said arcuate member tilted in a first direction, and (c) with said arcuate member tilted in a second direction.

7. A process for measuring improvement in the ocular tracking ability of a person undergoing motor perceptual training, comprising the steps of:
(a) providing an ocular-pursuit measuring instrument comprising:
(i) a first upstanding leg member;
(ii) a second upstanding leg member spaced from the first leg member;
(iii) connecting means connecting said first and second leg members;
(iv) vertically adjustable chin support means at the upper end of said first leg member, said support means being adapted to stably support said person's head; and
(v) an arcuate member pivotably mounted at its midpoint to the upper end of said second leg member in a manner such that said arcuate member may be pivoted about an axis passing through said midpoint perpendicular to the axis of said second leg member; wherein said arcuate member includes a graduated scale therealong;
(b) measuring the ocular tracking ability of said person with said instrument prior to administering motor perceptual training; said measuring comprising the steps of:
(i) positioning such person in a manner such that the person's chin is stably supported by said chin support means;
(ii) placing said arcuate member in a horizontal position;
(iii) testing said person's ocular tracking ability by moving a target along said arcuate member from said midpoint to measure smooth eye movement by such person following said target; said testing comprising the steps of:
(1) moving said target along said arcuate member from said midpoint until a first point of nystagmus is observed;
(2) returning said target to said midpoint;
(3) moving said target along said arcuate member from said midpoint, while measuring smooth eye movement, to a point which is less than said first point of nystagmus;
(4) returning said target to said midpoint;
(5) moving said target along said arcuate member from said midpoint, while measuring smooth eye movement, to a point which is one graduated unit farther than the point reached in step (3);
(6) repeating steps (4) and (5), increasing the distance said target is moved along said arcuate member by one graduated unit with each repetition until a second point of nystagmus is reached;
(iv) recording the number of units on said graduated scale between said midpoint and the maximum point where smooth eye movement was completed accurately;
(c) administering motor perceptual training to said person; and
(d) re-measuring the ocular tracking ability of said person following said training by repeating steps (b)(i) through (b)(iv).

8. A process in accordance with claim 7, wherein said arcuate member is semi-circular and has a radius of curvature in the range of about 20 inches.

9. A process in accordance with claim 7, wherein said scale on said arcuate member is graduated in units of 0.5 inch from said midpoint outwardly therealong.

10. A process in accordance with claim 7, wherein said first and second leg members are parallel to each other and are spaced from each other such that the distance between the subject and the arcuate member is about 20 inches.

11. A process in accordance with claim 7, wherein said leg member are vertically adjustable.

12. A process in accordance with claim 7, wherein said ocular tracking ability of said patient is measured (a) with said arcuate member in horizontal position, (b) with said arcuate member tilted 45° from horizontal in a first direction, and (c) with said arcuate member tilted 45° from horizontal in a second direction; wherein the scores from said tests are summed.

13. A process in accordance with claim 7, wherein said connecting means comprises a bar which is affixed to the lower end of each said leg member.

14. A process for diagnosing a person's need for motor perceptual training comprising the steps of:
(a) providing an ocular-pursuit measuring instrument comprising chin support means facing the midpoint of an arcuate member spaced therefrom; wherein said chin support means is adapted to stably support such person's head; wherein said arcuate member is pivotably mounted at its midpoint; and wherein said arcuate member includes a graduated scale therealong;
(b) positioning such person in a manner such that the person's chin is stably supported by said chin support means;
(c) placing said arcuate member in a horizontal position;
(d) testing the person's ocular tracking ability by moving a target along said arcuate member from said midpoint to measure smooth eye movement by such person following said target; and
(e) recording the number of units on said graduated scale between said midpoint and the maximum point where smooth eye movement was completed accurately.

15. A process in accordance with claim 14, wherein step (d) comprises:
    (i) moving said target along said arcuate member from said midpoint until a first point of nystagmus is observed;
    (ii) returning said target to said midpoint;
    (iii) moving said target along said arcuate member from said midpoint, while measuring smooth eye movement, to a point which is less than said first point of nystagmus;
    (iv) returning said target to said midpoint;
    (v) moving said target along said arcuate member from said midpoint, while measuring smooth eye movement, to a point which is one graduated unit farther than the point reached in step (iii);
    (vi) repeating steps (iv) and (v), increasing the distance said target is moved along said arcuate member by one graduated unit with each repetition until a second point of nystagmus is reached.

16. A process in accordance with claim 15, wherein said ocular tracking ability of such person is tested (a) with said arcuate member in horizontal position, (b) with said arcuate member tilted 45° from horizontal in a first direction, and (c) with said arcuate member tilted 45° in a second direction; wherein the scores from said tests are 17. A process in accordance with claim 1, wherein steps (d) and (e) are performed separately with respect to said person's left eye, right eye, and then both eyes together.

18. A process in accordance with claim 7, wherein step (b) is performed separately with respect to said person's left eye, right eye, and then both eyes together.

19. A process in accordance with claim 14, wherein steps (d) and (e) are performed separately with respect to said person's left eye, right, eye, and then both eyes together.

* * * * *